(12) United States Patent
Toh et al.

(10) Patent No.: US 6,592,601 B1
(45) Date of Patent: *Jul. 15, 2003

(54) CORNEAL SURGICAL APPARATUS

(75) Inventors: Minoru Toh, Aichi (JP); Katsuhiko Kozawa, Aichi (JP); Masahiro Sugimura, Aichi (JP)

(73) Assignee: Nidek Co., Ltd., Gamagori (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/281,959

(22) Filed: Mar. 31, 1999

(30) Foreign Application Priority Data

| Mar. 31, 1998 | (JP) | 10-125441 |
|---|---|---|
| Dec. 22, 1998 | (JP) | 10-363685 |
| Dec. 22, 1998 | (JP) | 10-363687 |

(51) Int. Cl.⁷ ............................................. A61B 17/32
(52) U.S. Cl. ..................................................... 606/166
(58) Field of Search ................................. 606/166, 167, 606/171, 172, 170

(56) References Cited

U.S. PATENT DOCUMENTS

| 4,662,370 A | 5/1987 | Hoffmann et al. |
|---|---|---|
| 4,903,695 A | 2/1990 | Warner et al. |
| 5,496,339 A | 3/1996 | Koepnick |
| 5,586,980 A | 12/1996 | Kremer et al. |
| RE35,421 E | 1/1997 | Ruiz et al. |
| 5,595,570 A | 1/1997 | Smith |
| 5,624,456 A | 4/1997 | Hellenkamp |
| 6,228,099 B1 * | 5/2001 | Dybbs .................... 606/166 |

FOREIGN PATENT DOCUMENTS

| JP | 11-19115 | 1/1999 |
|---|---|---|

OTHER PUBLICATIONS

Schwind, "Microkeratom, User Manual, Version 2.0", Herbert Schwind GmbH & Co. KG/Optical Instruments, pp. 1–44, (Feb. 1997).
Schwind, "Microkeratom, Service Manual", Herbert Schwind GmbH & Co. KG/Optical Instruments, pp. 1–34 (Mar. 1997).

* cited by examiner

*Primary Examiner*—Michael H. Thaler
(74) *Attorney, Agent, or Firm*—Finnegan, Henderson, Farabow, Garrett & Dunner LLP

(57) ABSTRACT

In a corneal surgical apparatus for incising a cornea of a patient's eye in a layered form, a blade is movably supported to a main body for lateral oscillation and rectilinear movement. Discrete motors are located within the main body for the lateral oscillation and the rectilinear movement of the blade, respectively. One of the motor is coupled to the blade through a feed screw, an attaching member threadingly engaged with the feed screw, and a hollow connecting member connected to the attaching member, whereas the other of the motor is coupled to the blade through gears, a spline shaft rotatably supported by the inside of the hollow connecting member and non-rotatably but slidably connected to one of the gears, and a converting mechanism for converting the rotation of the shaft to the lateral oscillation of the blade.

20 Claims, 5 Drawing Sheets

CORNEAL SURGICAL APPARATUS

BACKGROUND OF THE INVENTION

1. Field of the Invention

The present invention relates to a corneal surgical apparatus for incising the cornea of an eye of a patient in a layered form at the time of a keratorefractive surgery or the like.

2. Description of the Related Art

In recent years, attention has been focused on LASIK (laser in situ keratomileusis) surgery for effecting keratorefractive treatment wherein after a flap is formed by incising a corneal portion with a thickness of 150 $\mu$m ranging from the corneal epithelium to the corneal stroma with one end of the cornea remaining connected like a hinge, the corneal stroma is cut away or ablated in a refractive correction amount by excimer laser light, and the flap is then returned to its original position. In this LASIK surgery, a corneal surgical apparatus called a microkeratome is used to incise the cornea in a layered form.

Such microkeratome is available that has a suction ring vacuum-fixed to a portion of the cornea ranging from a corneal ring portion to the surface of the conjunctiva, a cornea applanating member for applanating the cornea flatly, and a blade which, while being oscillated in the lateral direction, is linearly moved or rotatively moved in a direction toward the hinge along a guide mechanism provided on the suction ring, so as to incise the cornea into a layered form with a substantially uniform thickness.

The guide mechanism is arranged such that a rack is provided on the suction ring, while a rotating gear meshing with the rack is provided on the blade side so that the blade is moved while being guided by the rack as the rotating gear is rotated. Another known guide mechanism is arranged such that the blade is moved along a guide groove provided on the suction ring.

In addition, the following mechanisms are also known: one in which the lateral oscillation of the blade and the movement of the blade toward the hinge are effected by a single motor provided in an apparatus body; one in which rotatively driving forces of two motors in a controller provided separately from the apparatus body are respectively transmitted to a blade oscillating mechanism and a blade moving mechanism in the apparatus body through two wires, so as to separately control the oscillation and movement of the blade; and one in which the oscillation speed and the translation speed of the blade can be variably set, respectively.

However, as for the microkeratome which has a guide mechanism or a gear mechanism on the suction ring, there are cases where the patient's eyelashes bite into the guide mechanism during a surgical operation to stop the movement of the blade. In this case, it is necessary to resume the operation after removing the eyelashes, but this imposes an adverse effect on the patient's eye. Further, a layered incision with an equal thickness cannot be realized by the re-operation. Since the guide mechanism causes abrasion dust, there is apossibility that the abrasion dust enters into the patient's eye if the guide mechanism is provided on the suction ring.

The characteristics of the cornea and the intraocular pressure differ depending on the patient's eye, but in the case of the microkeratome in which the lateral oscillation and movement of the blade are effected by one motor, it is difficult to optimize the relationship between the feeding movement and the lateral oscillation for obtaining a satisfactorily smooth surface as the incised surface.

In the case of the microkeratome in which the rotatively driving forces of two motors in a controller are transmitted to the blade oscillating mechanism and the blade moving mechanism through the two wires, the wires hinder the surgical operation.

In addition, unless the relationship between the set oscillation speed and the set translation speed of the blade is appropriate, the following problems can possibly occur. If the translation speed is excessively faster than the oscillation speed (the oscillation speed is excessively slower than the translation speed), the cut surface of the cornea may become nonuniform. On the other hand, if the translation speed is excessively,slower than the oscillation speed (the oscillation speed is excessively faster than the translation speed), frictional heat may occur on the cut surface, or extra time is needed until the incision is completed, so that the efficiency is poor.

SUMMARY OF THE INVENTION

In view of the above-described problems, it is an object of the present invention to provide a corneal surgical apparatus which eliminates the possibility of an interruption of surgery caused in connection with a guide mechanism and which permits a satisfactory surgical operation appropriate to the condition of the patient's eye without imposing an adverse effect on the patient's eye.

Another object of the present invention is to provide a corneal surgical apparatus which makes it possible to perform the incision of the cornea efficiently and satisfactorily by appropriately setting the oscillation speed and the translation speed of the blade.

To overcome the above-descirbed objects, the present invention is characterized by the following features.

(1) A corneal surgical apparatus for incising a cornea of a patient's eye in a layered form using a blade, includes:

a blade moving shaft supported rotatably and axially movably, wherein axial movement of the blade moving shaft causes the blade to advance or retract and rotation of the shaft causes the blade to make lateral oscillation;

first driving means, having a first motor, for axially moving the blade moving shaft by rotation of the first motor; and second driving means, having a second motor, for rotating the blade moving shaft by rotation of the second motor.

(2) The corneal surgical apparatus according to (1), wherein the first driving means includes:

a feed screw portion which is rotated by the rotation of the first motor; and a connecting member meshing with the feed screw portion and rotatably holding the blade moving shaft.

(3) The corneal surgical apparatus according to (1), wherein the second driving means includes:

a rotation transmitting member for holding the blade moving shaft axially slidably, and rotating the blade moving shaft by the rotation of the second motor.

(4) The corneal surgical apparatus according to (3), wherein the blade moving shaft includes a spline shaft having a first portion circular in section and a second portion noncircular in section, and the second portion is slidable with respect to the rotation transmitting member.

(5) The corneal surgical apparatus according to (1), further includes:

controlling means for controlling the first driving means so as to cause the blade to advance or retract at a predetermined moving speed, and controlling the second driving means so as to oscillate the blade at a predetermined oscillation speed.

(6) The corneal surgical apparatus according to (5), further includes:

setting means for variably setting at least one of the moving speed and the oscillation speed.

(7) The corneal surgical apparatus according to (6), further includes:

determining means for determining whether or not a relationship between the moving speed and the oscillation speed is appropriate.

(8) The corneal surgical apparatus according to (7), further includes:

storing means for storing a relative allowable setting range of the moving speed and the oscillation speed, wherein the determining means determines whether or not the relationship between the moving speed and the oscillation speed is appropriate on the basis of the allowable setting range stored in the storing means.

(9) The corneal surgical apparatus according to (1), further includes;

setting means for variably setting two parameters which respectively correspond to a moving speed of the blade defined by the first driving means and an oscillation speed of the blade defined by the second driving means;

storing means for storing a relative allowable setting range of the moving speed and the oscillation speed;

limiting means for limiting the allowable setting range of one of the parameters on the basis of both the allowable setting range stored in the storing means and the other of the parameters set by the setting means; and controlling means for controlling the first driving means and the second driving means on the basis of the parameters set by the setting means.

(10) The corneal surgical apparatus according to (1), further includes:

first setting means for variably setting one of two parameters which respectively correspond to a moving speed of the blade defined by the first driving means and an oscillation speed of the blade defined by the second driving means;

storing means for storing an optimum combination of the moving speed and the oscillation speed;

second setting means for setting the other of the parameters on the basis of both the combination stored in the storing means and the one of the parameters set by the first setting means; and, controlling means for controlling the first driving means and the second driving means on the basis of the parameters set by the first setting means and the second setting means.

(11) The corneal surgical apparatus according to (1), further includes:

position detecting means for detecting a position of the blade; and controlling means for controlling at least one of a moving speed of the blade defined by the first driving means and an oscillation speed of the blade defined by the second driving means on the basis of position information obtained by the position detecting means.

(12) The corneal surgical apparatus according to (1), further includes:

changeover means for changing over at least one of a moving speed of the blade defined by the first driving means and an oscillation speed of the blade defined by the second driving means in association with how degree a surgical operation proceeds.

(13) The corneal surgical apparatus according to (1), further includes:

a suction ring for abutment against the partient's eye;

sucking means for sucking air in a gap formed between the suction ring and the patient's eye to fix the suction ring onto the patient's eye;

pressure detecting means for detecting air pressure in the gap which varies due to the suction by the sucking means; and controlling means for controlling at least one of the first driving means and the second driving means on the basis of pressure information detected by the pressure detecting means.

(14) The corneal surgical apparatus according to (13), further includes:

suction controlling means for controlling the sucking means on the basis of the pressure information detected by the pressure detecting means.

(15) A corneal surgical apparatus for incising a cornea of a patient's eye in a layered form using a blade, includes:

oscillating means for laterally oscillating the blade;

moving means for moving the blade in an incising direction;

setting means for variably setting at least one of a moving speed and a oscillation speed of the blade; and determining means for determining whether or not a relationship between the moving speed and the oscillation speed is appropriate.

(16) The corneal surgical apparatus according to (15) further includes:

notifying means for notifying an operator of a result of determination by the determining means.

(17) The corneal surgical apparatus according to (15), further includes:

controlling means for controlling the oscillating means and the moving means on the basis of a result of determination by the determining means.

(18) The corneal surgical apparatus according to (15), further includes:

storing means for storing a relative allowable setting range of the oscillation speed and the moving speed, wherein the determining means determines whether or not the relationship between the oscillation speed and the moving speed is appropriate on the basis of the allowable setting range stored in the storing means.

(19) The corneal surgical apparatus according to (18), further includes:

displaying means for displaying the allowable setting range when it is determined by the determining means that the relationship between the oscillation speed and the moving speed is inappropriate.

(20) The corneal surgical apparatus according to (18), further includes:

resetting means for resetting at least one of the oscillation speed and the moving speed on the basis of the allowable setting range when it is determined by the determining mans that the relationship between the oscillation speed and the moving speed is inappropriate.

(21) A corneal surgical apparatus for incising a cornea of a patient's eye in a layered form using a blade, includes
  oscillating means for laterally oscillating the blade;
  moving means for moving the blade in an incising direction;
  setting means for variably setting two parameters which respectively correspond to an oscillation speed of the blade defined by the oscillating means and a moving speed of the blade defined by the moving means;
  storing means for storing a relative allowable setting range of the oscillation speed and the moving speed;
  limiting means for limiting the allowable setting range of one of the parameters on the basis of both the allowable setting range stored in the storing means and the other of the parameters set by the setting means; and
  controlling means for controlling the oscillating means and the moving means on the basis of the parameters set by the setting means.

(22) The corneal surgical apparatus according to (21), wherein the limiting means determines the allowable setting range of one of the parameters based on the other of the parameters thus set, and displays the thus determined allowable setting range.

(23) The corneal surgical apparatus according to (21), wherein the limiting means determines the allowable setting range of one of the parameters based on the other of the parameters thus set, and permits the setting means to set the one of the parameters within the thus determined allowable setting range.

(24) A corneal surgical apparatus for incising a cornea of a patient's eye in a layered form using a blade, comprising:
  oscillating means for laterally oscillating the blade;
  moving means for moving the blade in an incising direction;
  first setting means for variably setting one of two parameters which respectively correspond to an oscillation speed of the blade defined by the oscillating means and a moving speed of the blade defined by the moving means;
  storing means for storing an optimum combination of the oscillation speed and the moving speed;
  second setting means for setting the other of the parameters on the basis of both and the combination stored in the storing means and the one of the parameters set by the first setting means; and
  controlling means for controlling the oscillating means and the moving means on the basis of the parameters set by the first setting means and the second setting means.

(25) A corneal surgical apparatus for incising a cornea of a patient's eye in a layered form, includes:
  a main body;
  a blade movable with respect to the main body; first and second independent motors located within the main body;
  a feed screw associated with the first motor;
  an attaching member threadingly engaged with the feed screw;
  a connecting member connecting the attaching member to the blade; and
  a rotating shaft associating the second motor with the blade.

(26) The corneal surgical apparatus according to (25), wherein the second motor is supported by the main body.

(27) The corneal surgical apparatus according to (26), wherein the rotating shaft is coupled to the second motor through a spline coupling.

(28) The corneal surgical apparatus according to (25), wherein the second motor is supported by the attaching member.

(29) The corneal surgical apparatus according to (25), wherein the feeding screw and the attaching member are located within the main body.

(30) A corneal surgical apparatus for incising a cornea of a patient's eye in a layered form using a blade, includes:
  a first motor associated with the blade for oscillation of the blade;
  a second motors associated with the blade for rectilinear movement of the blade; and
  an input unit by which rotational speeds of the first and second motors can be set independently from each other.

(31) A corneal surgical apparatus according to (30), further includes:
  a control unit, which determines whether the rotational speeds independently set by the input unit are appropriate.

(32) A corneal surgical apparatus according to (30), further includes:
  a memory which stores an allowable relationship between the rotational speeds of the first and second motors; and
  a control unit, which retrieves the allowable relationship from the memory when at least one of the rotational speeds is set by the input unit.

The present disclosure relates to the subject matter contained in Japanese patent application Nos. Hei. 10-125441 (filed on Mar. 31, 1998), Hei. 10-363685 (filed on Dec. 22, 1998) and Hei. 10-363687 (filed on Dec. 22, 1998) which are expressly incorporated herein by reference in their entireties.

DESCRIPTION OF THE PREFERRED EMBODIMENT

First Embodiment

Referring to the accompanying drawings, a description will be given of a first embodiment of the present invention.

Figure 1:
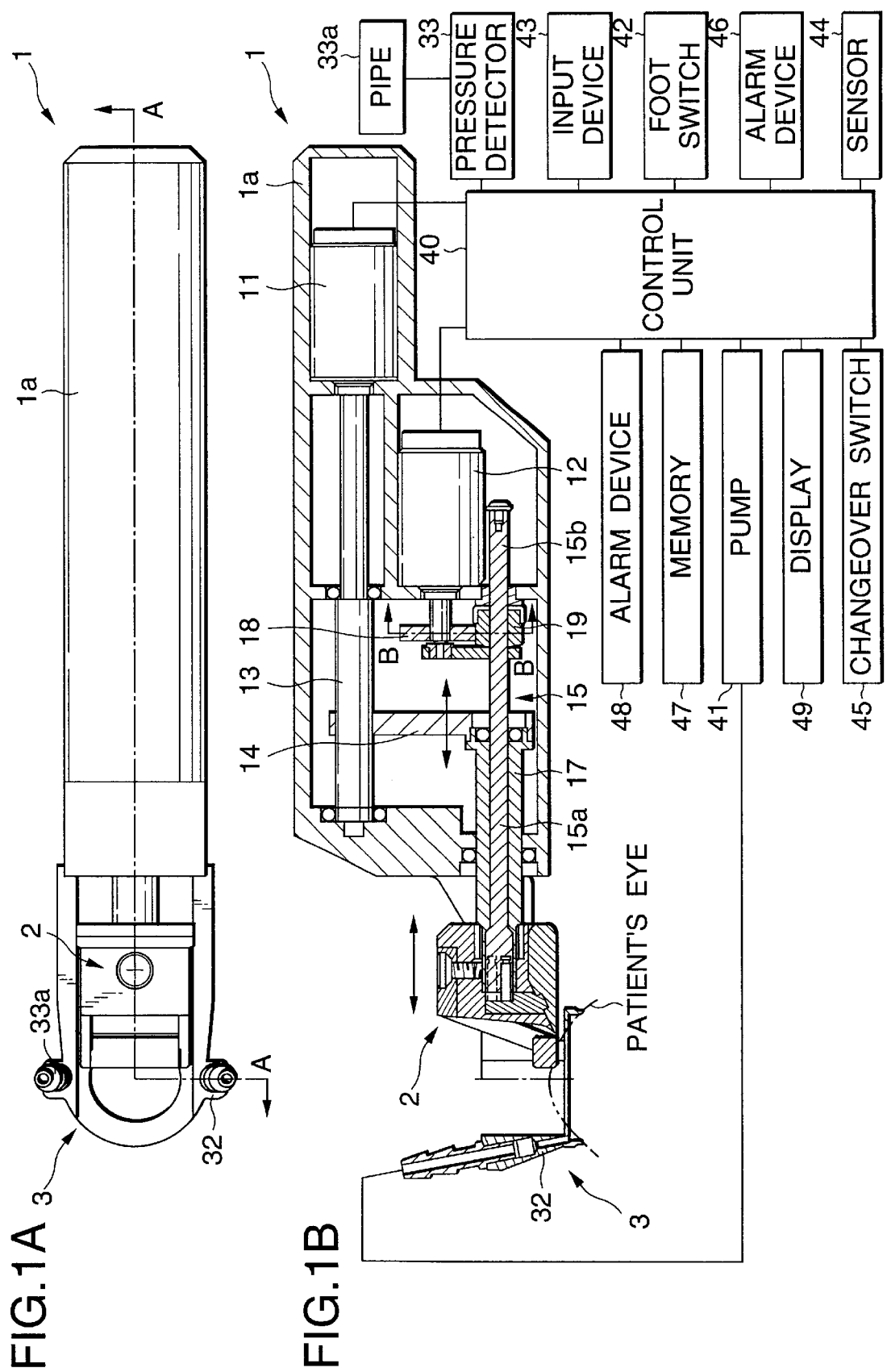
FIG. 1A is a plan view of a corneal surgical apparatus in accordance with a first embodiment of the present invention.
FIG. 1B is a cross-sectional view taken along line A—A of FIG. 1A, illustrating a schematic diagram of a control system.

FIG. 1A is a top view of a corneal surgery apparatus body in accordance with the first embodiment of the present invention, and FIG. 1B is a cross-sectional view taken along line A—A in FIG. 1A and illustrates the schematic configuration of a control system.

Reference numeral 1 denotes a main body of the microkeratome, and numeral 1a denotes a grip portion which is to be held by an operator during a surgery. A suction unit 3 for fixing the apparatus to the patient's eye and a cutting unit 2, which has a blade 20 (which will be described later) for incising the cornea and is adapted to move rectilinearly on the suction unit 3, are provided on the front side (left-hand side in the drawing) of the main body 1.

A feed motor 11 for rectilinearly moving or translating the cutting unit 2 in the incising direction and an oscillating motor 12 for imparting lateral oscillations to the blade 20 are fixedly provided in the main body 1. A reed screw 13 is coupled to a rotating shaft of the motor 11. The feed screw 13 has a threaded portion corresponding in length to a distance by which the cutting unit 2 is translated. An attaching member 14, to which a tubular connecting member 17 connected to the cutting unit 2 is fixed, is threadedly engaged on the screw 13. As the motor 11 is rotated forwardly or reversely, the connecting member 17 moves forwardly or backwardly through the screw 13 and the attaching member 14, thereby causing the cutting unit 2 to move forwardly or backwardly. A rotating shaft 15 is held by the connecting member 17 in such a manner as to be rotatable and movable axially (forwardly or backwardly). An eccentric shaft 16 is embedded on a distal end of the rotating shaft 15 at a position offset from the center of rotation, and the eccentric shaft 16 imparts lateral oscillations to the blade 20 (which will be described later).

Figure 2:
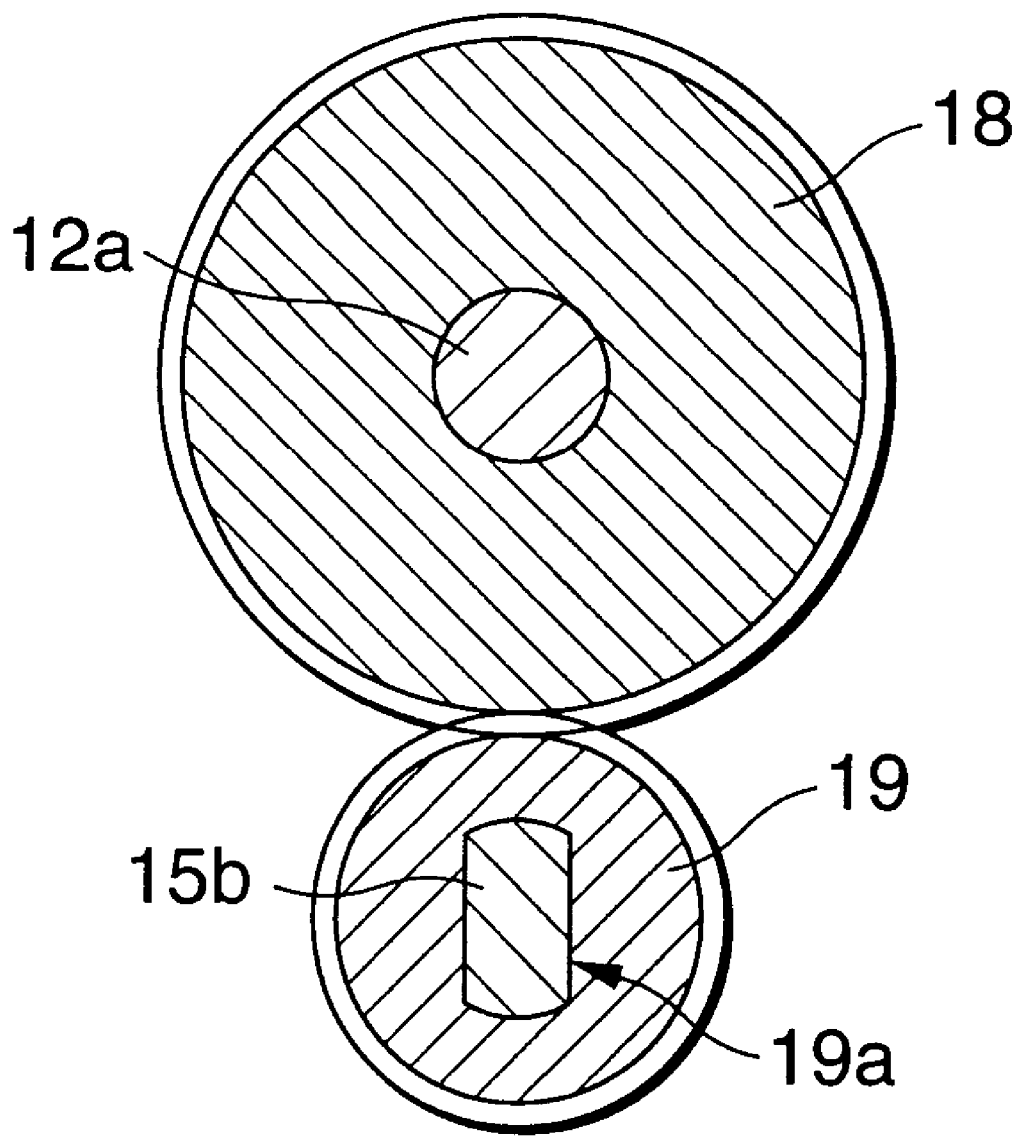
FIG. 2 is a cross-sectional view taken along line B—B of FIG. 1B, illustrating a spline shaft of the apparatus in accordance with the first embodiment of the present invention.

A so-called spline shaft is used as the rotating shaft 15, and its rotating mechanism is arranged as follows. A front portion 15a of the rotating shaft 15 is formed into a circular cross-sectional shape, and rotatable with respect to the inside of the connecting member 17 through a bearing. A rear portion 15b of the rotating shaft 15 is formed entirely into an oval cross-sectional shape which is noncircular, as shown in FIG. 2 (a cross-sectional view taken along line B—B of FIG. 1B). A drive gear 18 is attached to a rotating shaft 12a of the motor 12, and a rotating gear 19 which is held rotatably within the main body 1 meshes with the drive gear 18. A shaft hole 19a, through which the rear portion 15b of the rotating shaft 15 is inserted, is provided in the center of rotation of the rotating gear 19, and the shaft hole 19a is formed into the same oval cross-sectional shape as that of the rear portion 15b (see FIG. 2). With this arrangement, the rotation of the motor 12 is transmitted to the rotating shaft 15 through the drive gear 18 and the rotating gear 19. As the motor 11 is driven, the rotating shaft 15 is slid relative to the shaft hole 19a of the rotating gear 19 to make the translational motion together with the connecting member 17.

The use of the spline shaft makes it possible to transmit the lateral oscillation to the blade 20 through the rotational motion of the rotating shaft 15 without any translation of the motor 12 even if the translational motion of the cutting unit 2 accompanies thereto. Namely, since the motor 12 can be fixed to the main body 1, no load of the motor 12 is applied to the attaching portion 14, thereby making it possible to reduce the load applied to the motor 11.

In addition, since the rotating shaft 15 also functions as a guide for the translational motion, it is unnecessary to provide a guide on a suction ring 31 (which will be described later). Furthermore, since most contact portions which may cause the abrasion dust are arranged inside the main body 1 together with the motors, the scattering of abrasion dust due to the high speed rotation of the rotating shaft 15 takes place inside the main body 1. Thus, the patient's eye is protected from the abrasion dust.

Figure 3A:
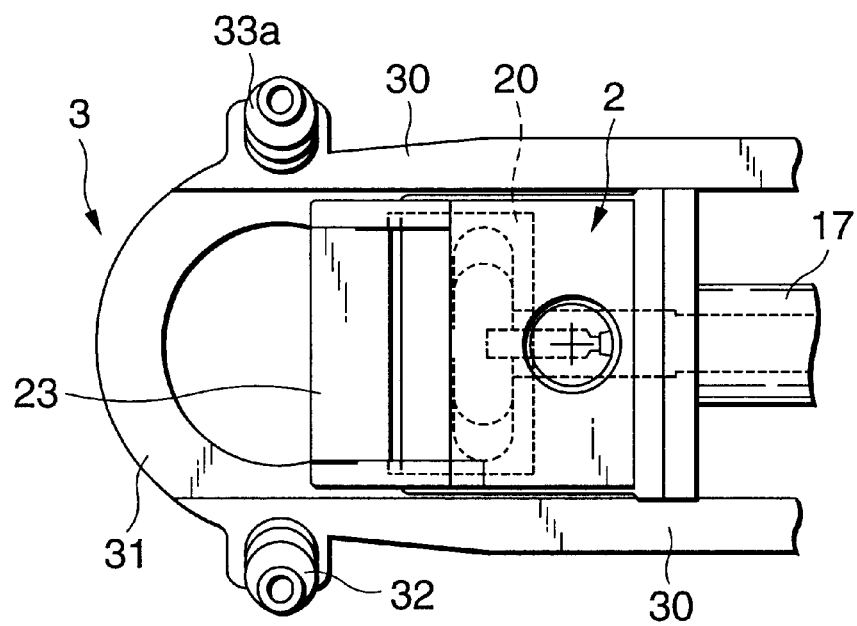
FIGS. 3A and 3B are enlarged explanatory diagrams of a cutting unit and a suction unit of the apparatus in accordance with the first embodiment.
Figure 3B:
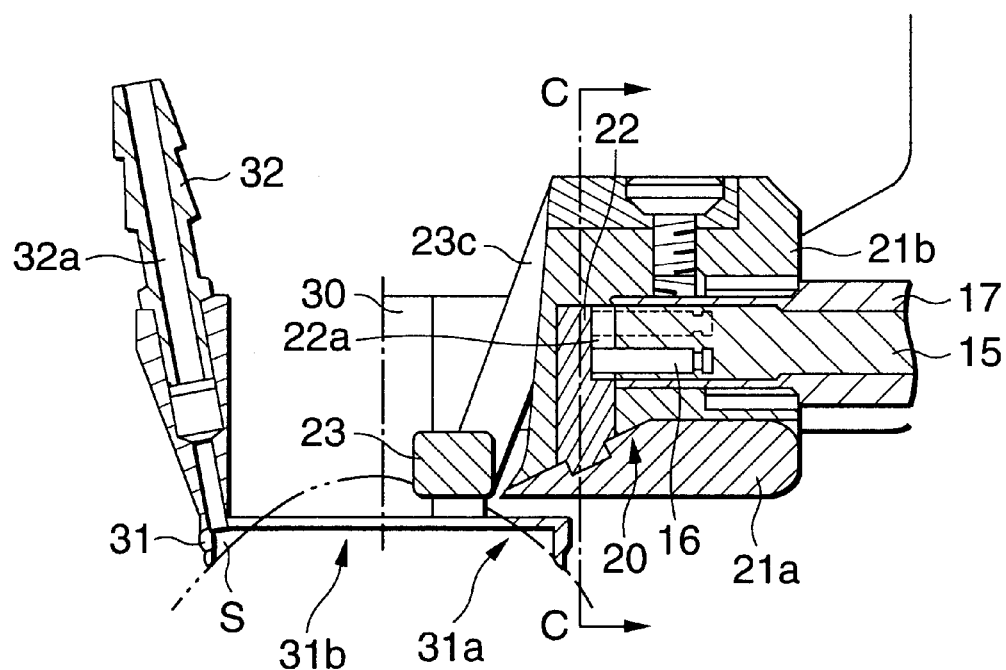
Figure 4:
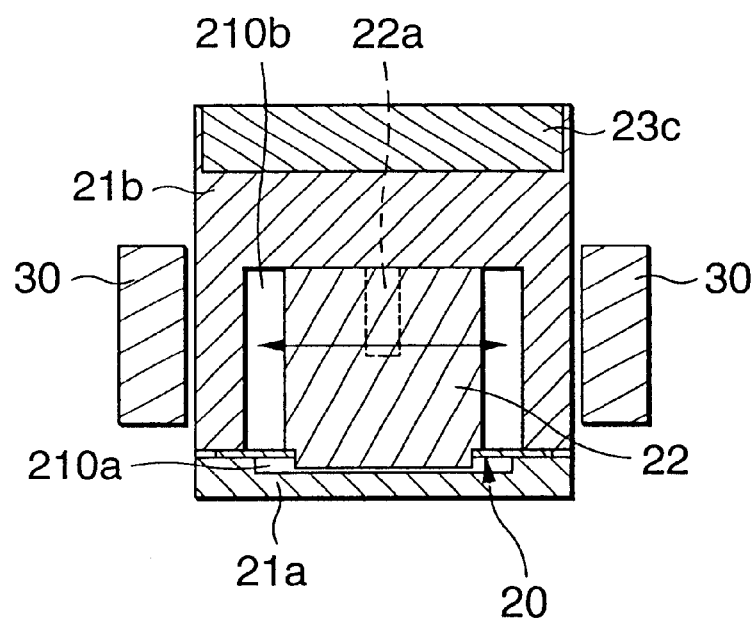
FIG. 4 is a cross-sectional view taken along line C—C of FIG. 3B, illustrating the cutting unit of the apparatus in accordance with the first embodiment.

Referring next to FIGS. 3A, 3B and 4, a description will be given of the arrangements of the cutting unit 2 and the suction unit 3. FIGS. 3A and 3B are enlarged views of the cutting unit 2 and the suction unit 3 shown in FIGS. 1A and 1B. FIG. 4 is cross-sectional view taken along line C—C of FIG. 3B.

The cutting unit 2 is comprised of the blade 20 for corneal incision; a blade holder 21a and a holder block 21b for holding the blade 20 in such a manner as to permit lateral oscillations; an oscillation transmitting member 22 for transmitting the lateral oscillations generated by the eccentric shaft 16 to the blade 20; and a cornea applanating portion 23 fixed to the block 21b by an attaching member 23c. A rotation hole into which the rotating shaft 15 is inserted is provided inside the block 21b, and a tip portion of the connecting member 17 is fixed thereto.

A metal blade having a blade edge of stainless steel, steel, or the like or a mineral blade having a blade edge of diamond, sapphire or the like is used as the blade 20, and the blade 20 is held between the holder 21a and the block 21b at an appropriate angle with respect to the horizontal plane in such a manner as to be capable of undergoing lateral oscillations. On the holder 21a side, a shallow recess 210a is formed at a portion where the blade 20 is placed, and the lateral width of the recess 210a is set to be larger than the oscillating width for the lateral oscillations of the blade 20.

The transmitting member 22 is secured to the blade 20, and is movable in the lateral direction within a receiving groove 210b formed in the block 21b. A vertical groove 22a for engagement with the eccentric shaft 16 is formed in the transmitting member 22. When the rotating shaft 15 is rotated by the rotative driving of the motor 12, the eccentric shaft 16 attached to the tip of the rotating shaft 15 and engaged with the vertical groove 22a applies a lateral driving force to the transmitting member 22. This causes the blade 20 to oscillate laterally together with the transmitting member 22.

The applanating portion 23 is provided on the front side (left-hand side in the drawing) of the blade 20 so as to flatly applanate the cornea of the patient's eye in advance of the corneal incision by the blade 20 as the cutting unit 2 is moved forwardly. Since the blade 20 incises the cornea thus applanated flatly by the applanating portion 23, a flap of a uniform layer is formed.

In this embodiment, the distance between the edge of the blade 20 attached to the holder 21a and the lower surface of the applanating portion 23 is set to be about 150 microns ($\mu$m) so that the corneal epithelium can be incised with this thickness in a layered form.

The suction unit 3 includes a fixing member 30, a suction ring 31, and a suction pipe 32. The suction ring 31 is fixed to the main body 1 by the fixing member 30. The suction ring 31 has a substantially hollow cylindrical shape (a substantially U-shape in section), which has a circular recessed portion 31a adapted to abut against the patient's eye, and an opening 31b concentric to the recessed portion 31a. When the suction ring 31 is mounted on the patient's eye in place for surgery, the cornea of the patient's eye projects upward from the opening 31b, and a lower end portion of the suction ring 31 and an opening end portion (a periphery) of the opening 31b are caused to abut against the patient's eye to define a space S for suction.

The suction pipe 32 is embedded in the suction ring 31, and connected through an unillustrated vacuum tube to a pump 41. A suction passage 32a provided inside the suction pipe 32 communicates with the recessed portion 31a, and as the air inside the space S is sucked and discharged by the pump 41 through the passage 32a, the suction ring 31 is vacuum-fixed to the patient's eye. In this fixation, as the operator holds the grip portion 1a of the main body 1, the positioning of the opening 31b can be facilitated, and the apparatus can be held stably.

In addition, a pipe 33a for pressure detection is embedded in the suction ring 31, and the pipe 33a is connected to a pressure detector 33 through an unillustrated tube. The detector 33 detects the air pressure inside the space S sucked by the pump 41. A control unit 40 controls the operation of the apparatus on the basis of the air pressure detected by the detector 33. If the air pressure within the space S is not set to be a sufficiently negative pressure due to the presence of a gap between the suction ring 31 and the patient's eye or due to the clogging of the passage 32a or the like with a foreign object, there is a possibility that the corneal rigidity is not secured appropriately. For this reason, a predetermined value is preset as an upper limit of the air pressure required to secure the corneal rigidity to a certain extent, and if the detected air pressure is more positive than this predetermined value of the upper limit, the operation of the apparatus (the feeding or oscillation of the blade 20) is stopped (the starting of the apparatus is inhibited if it is detected before the surgery, and the operation of the apparatus is stopped if it is detected during the surgery). In this case, the operator stops the input of a drive instruction signal by a foot switch 42, and checks the state of abutment of the suction ring 31, the state of clogging of the passage 32a, and the like. When the detected air pressure reaches a level more negative than the predetermined pressure of the upper limit, and the operator reinputs the drive instruction signal by the foot switch 42, the apparatus is able to start or resume the operation. For convenience, an alarm device 46 maybe used to visually or audibly notify the operator of the fact that the detected air pressure has reached a level more negative than the predetermined value of the upper limit. For example, a buzzer may be provided to continuously generate a sound if the detected air pressure is at a level more positive than the predetermined value of the upper limit, and stop the generation of the sound if the detected air pressure reaches a level more negative than the predetermined value of the upper limit (to the contrary, the buzzer may be designed to generate a sound for a fixed time period from a time point at which the negative pressure has been reached). Furthermore, the apparatus may be designed such that it become operable to start the incision after the detected air pressure has reached a level more negative than the predetermined value of the upper limit.

On the other hand, the excessively negative air pressure within the space S caused due to an excessively long suction time or the like is not preferable since the intraocular pressure of the patient's eye becomes too high. For this reason, a predetermined value is preset as a lower limit of the air pressure to avoid such a situation. That is, the operation of the apparatus is stopped if the detected air pressure has reached a level more negative than the predetermined value of this lower limit. This makes it possible to perform the surgery without imposing the adverse effect on the patient's eye.

In addition, the predetermined values of the upper and lower limits for the air pressure as described above may be preset as fixed values, or may be variably set by the operator using an unillustrated switch or the like.

The control unit 40 is connected to the detector 33, the foot switch 42, and the like. The control Unit 40 controls the operation of the motors 11 and 12 and the pump 41. Reference numeral 43 designates an input unit by which the oscillation speed of the blade 20, the feeding speed of the blade 20 and so on can be set and input. As the input unit 43, Switches may be provided for changing the rotational speeds of the motors 11 and 12 in a stepwise manner to determine the oscillation speed and the feeding (translation) speed of the blade 20, respectively. Variable resisters may be provided for consecutively changing the rotational speeds of the motors 11 and 12, respectively. Each of these may be provided on the main body 1 side. The details of the input unit 43 will be described later.

Figure 5:
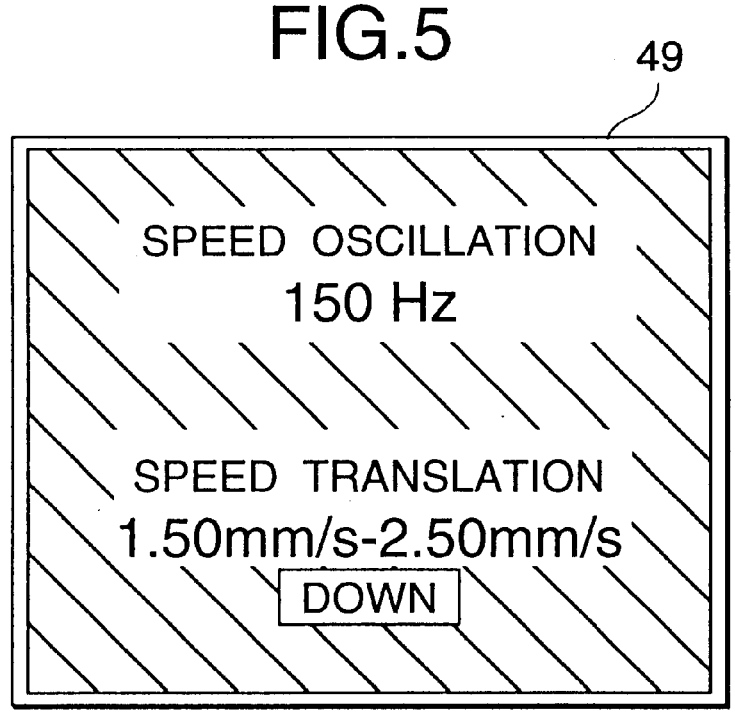
FIG. 5 is an example of display showing an allowable setting range of a translation speed when an oscillation speed is set.

Hereafter, a description will be given of the operation of the apparatus having the above-described configuration. First, the operator sets the oscillation speed and the translation speed of the blade 20, respectively, by operating the input device 43. A relative allowable setting range of the oscillation speed and the translation speed is stored in a memory 47 connected to the control unit 40 in the form of a table or calculation formula. The control unit 40 determines whether or not the set translation speed is within the allowable setting range with respect to the set oscillation speed. If it is determined that the set translation speed is within the allowable setting range, then an alarm 48, i.e., an error lamp, is not turned on, and the operation of a foot switch 42 causes the motor 11 and the motor 12 to be rotatively driven. If it is determined that the set translation speed is outside the allowable setting range, the alarm 48, i.e., the error lamp, is turned on. In this case, the control unit 40 inhibits the rotative driving of the motors by not accepting a drive instruction signal from the foot switch 42, or by not issuing drive signals to the motors 11 and 12, or by locking the motors 11 and 12. Concurrently, the control unit 40 drives a display 49 to display the allowable setting range of the translation speed with respect to the set oscillation speed (see FIG. 5). Consequently, the operator is able to reset the translation speed that falls within the allowable setting range. In addition, the notification of an error by the alarm 48 may be effected audibly.

The determination as to whether or not the rotative driving of the motors 11 and 12 can be started may be made on a determination as to whether or not the set oscillation speed is within the allowable setting range with respect to the set translation speed. In this case, if it is determined that the set oscillation speed is outside the allowable setting range, the control unit 40 drives the display 49 to display the allowable setting range of the oscillation speed with respect to the set translation speed. Furthermore, in either case where the oscillation speed or translation speed is set as the criterion, the control unit 40 may drive the display 49 to display both the allowable setting ranges of the oscillation speed and the translation speed so that the operator can reset both of the speeds.

Further, only the translation speed may be set with the oscillation speed be fixed (the memory 47 stores only the allowable setting range of the translation speed with respect to the fixed oscillation speed, and the display 49 displays the allowable setting range of the translation speed), or otherwise, only the oscillation speed may be set with the translation speed be fixed (the memory 47 stores only the allowable setting range of the oscillation speed with respect to the fixed translation speed, and the display 49 displays the allowable setting range of the oscillation speed).

Still further, if it is determined that the set translation speed is outside the allowable setting range with respect to the set (or fixed) oscillation speed, the control unit 40 may automatically reset a value which is closest to the set translation speed within the allowable setting range. It goes without saying that this also applies to a case where the oscillation speed and the translation speed are reversed.

As another method, if the oscillation speed is set first by the input device 43, the control unit 40 retrieves an allowable setting range of the translation speed with respect to the set oscillation speed, and then drives the display 49 to display the thus retrieved allowable setting range of the translation speed, thereby permit the operator to set the translation speed within the allowable setting range while reviewing the display. The input device 43 or the control unit 40 may be designed such that values outside the thus retrieved allowable setting range of the translation speed cannot be set. In this case, if a value outside the allowable setting range is set, the set signal cannot be accepted, and an error is displayed on the display 49 (or an error is notified by the alarm 46 or 48).

As still another method, if the oscillation speed is set first by the input device 43, the control unit 40 may retrieves an optimum value of the translation speed with respect to the set oscillation speed based on the table or calculation formula stored in the memory 47, and set the retrieved optimum value as the translation speed. In addition, it goes without saying that the oscillation speed and the translation speed may be reversed in these modifications.

After the oscillation speed of the blade 20 and the translation speed of the blade 20 have been set, the operator, while confirming the state of inclination of the suction ring 31 (main body 1), the position of the pupillary center, and the like on the basis of a mark that has been preliminarily applied on the patient's cornea using an instrument such as a marker, aligns the center of the opening 31*b* with the pupillary center, and disposes the suction ring 31 on the patient's eye.

After installation of the suction ring 31, the operator, while keeping the position and the posture of the main body 1, Operates the pump 41 to suck the air in the space S between the suction ring 31 and the patient's eye to thereby decrease the air pressure (toward the negative pressure). When the air pressure in the space S is decreased to a fixed value (when it reaches a sufficient negative pressure), the operation of the pump 41 is controlled by the control unit 40 so as to maintain that air pressure and vacuum-fix the suction ring 31 onto the patient's eye.

After completion of the fixation of the apparatus, the operator operates the foot switch 42 to rotatively drive the motor 11 and the motor 12. The control unit 40 controls, upon reception of the drive instruction signal from the foot switch 42, the rotational drive of the motor 12 to laterally oscillate the blade 20 at the oscillation speed thus set through the above-described method (or at the fixed oscillation speed). Since the blade 20 undergoes one oscillation per one revolution of the rotating shaft 15, the oscillation speed of the blade 20 can be controlled easily by changing the rotational speed of the motor 12 while taking into account a gear ratio between the drive gear 18 and the rotational gear 19.

Similarly, the control unit 40 controls the rotational drive of the motor 11 to translate or rectilinearly move the cutting unit 2 toward the hinge at the translation speed thus set through the above-described method (or at the fixed translation speed). Concurrently, the rotating shaft 15 slides in the advancing direction integrally with the cutting unit 2 while making rotational motion for imparting lateral oscillations to the blade 20.

Under the independent control of the motors 11 and 12 as described above, the blade 20 gradually incises the cornea of the patient's eye consecutively applanated flatly by the applanating portion 23. The surgery proceeds in this manner. Since the guide mechanism is not provided on the suction ring 31, the cutting unit 2 is moved smoothly without the generation of dust and the biting of the eyelashes during this surgery.

When the flap formation is complete, that is, the edge of the blade 20 has incised the cornea with the hinge portion left, the motor 11 is rotated reversely to return the cutting unit 2 to its initial position. For this return operation, the rotation of the motor 12 is only stopped using the independent control of the motors 11 and 12, to thereby withdraw or remove the blade 20 from the flap while avoiding the unnecessary oscillation of the blade 20. This reduces the possibility that the flap thus formed is cut off during the course of the return operation.

After the cutting unit 2 is returned to its initial position, the air is introduced into the space S to release the suction, and the apparatus is removed. Subsequently, a refractive correction amount of the corneal stroma is ablated and removed using laser light, and then the flap is returned to its original position, thereby completing the surgery.

As the shape of the rear portion 15*b* of the rotating shaft 15 described above, it is possible to adopt such a cross-sectional shape as to have a plurality of grooves or the like extending in the axial direction. A sliding key may be used instead of the spline shaft.

In addition, a detector such as a sensor 44 for detecting the position of the blade 20 in the feeding direction may be provided instead of the input device 43 so that the translation speed and the oscillation speed may be controlled on the basis of the detected position of the blade 20. For example, since the incision is relatively difficult at the corneal incision starting position (i.e. at the initial stage of the corneal incision), the control may be performed such that the translation speed is made slow at the initial stage, and then the translation speed is made faster from a certain position at which the sensor 44 detects the fact that the incision has progressed to a certain extent. Furthermore, the translation speed and the oscillation speed of the blade 20 may be controlled using a changeover switch 45 or the like for changing over the translation speed and the oscillation speed of the blade 20 in a plurality of stages. That is, the operator may manually changeover the translation speed and the oscillation speed of the blade 20 using the changeover switch 45 depending on the progress of the surgical operation. It goes without saying that the input device 43, the sensor 44 and the changeover switch 45 can be used in combination with each other. For example, after the translation speed and the oscillation speed are set by the input device 43, the position of the blade is detected by the sensor 44 or the changeover of the switch 45 is effected to control the translation speed and the oscillation speed within the allowable setting range determined by the input device 43.

SECOND EMBODIMENT

Figures 6A, 6B:
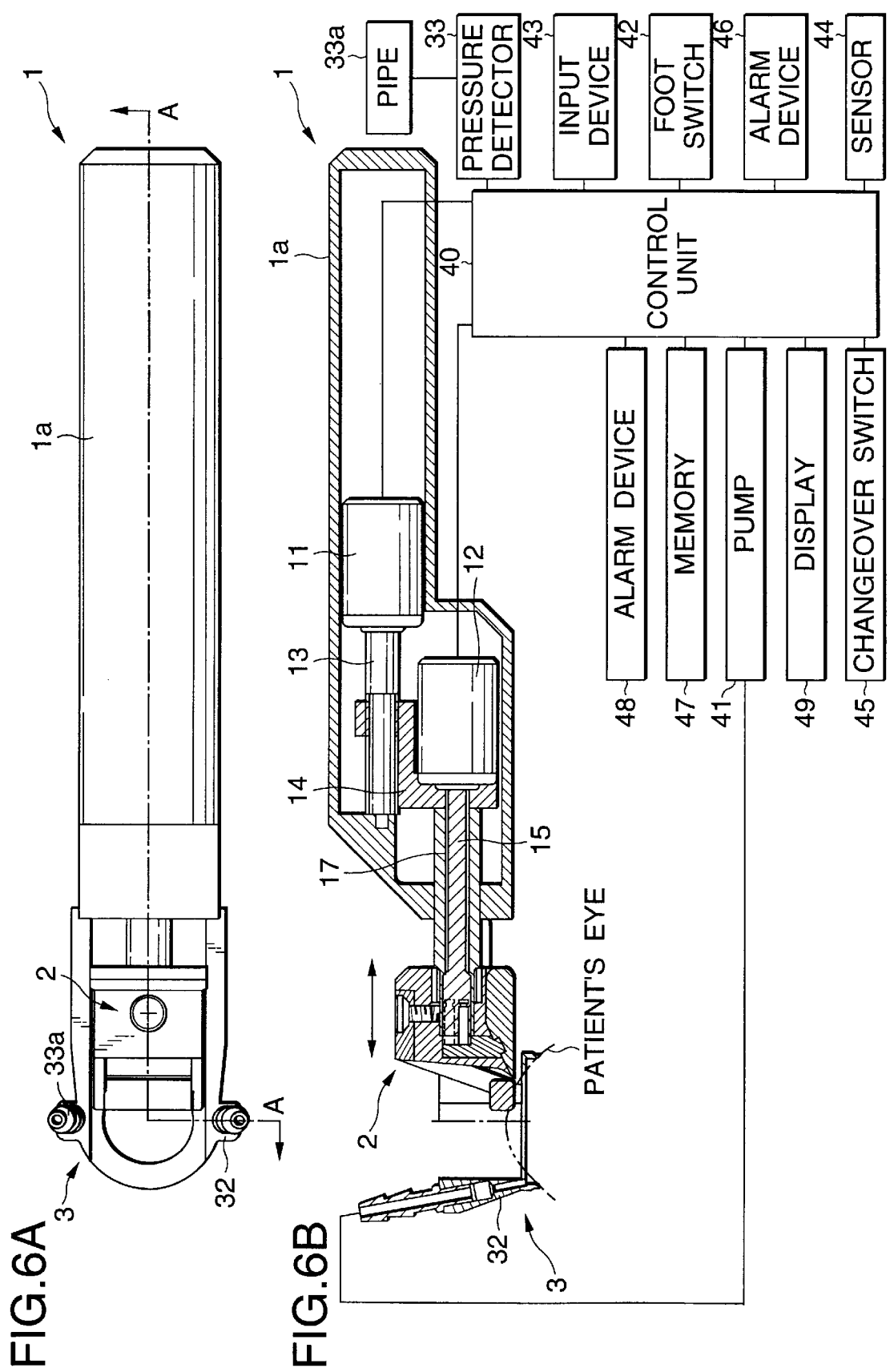
FIG. 6A is a plan view of a corneal surgical apparatus in accordance with a second embodiment of the present invention.
FIG. 6B is a cross-sectional view taken along line A—A of FIG. 6A, illustrating a schematic diagram of a control system.

Referring now to FIGS. 6A and 6B, a description will be given of a second embodiment of the present invention. FIG. 6A is a top view of a corneal surgical apparatus in accordance with the second embodiment of the present invention. FIG. 6B is a cross-sectional view taken along line A—A of FIG. 6A and illustrates a schematic configuration of a control system. In the following description and in these drawings, the same reference numerals as those of the first embodiment denote the same or functionally equivalent component parts.

A feed screw 13 is coupled to a rotating shaft of the motor 11, which has a threaded portion corresponding in length to the rectilinear movement or travel of the cutting unit 2. The motor 11 is fixedly provided within the main body 1. An attaching member 14 is threadedly engaged with the screw 13. The motor 12 as well as a connecting member 17 for connecting the motor 12 and the cutting unit 2 are fixed to the attaching member 14. As the motor 11 is rotated forwardly or reversely, the motor 12 and the connecting member 17 move forwardly or backwardly through the screw 13 and the attaching member 14, thereby causing the cutting unit 2 to move forwardly or backwardly. Further, a rotating shaft 15 is rotatably held by the connecting member 17. An eccentric shaft 16 is embedded on a distal end of the rotating shaft 15 at a position offset from the center of rotation, and the eccentric shaft 16 imparts lateral oscillations to the blade 20.

Thus, the second embodiment does not employ the spline shaft as the rotating shaft 15, and is designed such that the motor 12 is moved in connection with the translational motion of the cutting unit 2. Accordingly, the load or weight of the motor 12 is applied to the attaching member 14, and therefore more power is required for the motor 11 in comparison with the first embodiment. However, since the second embodiment can dispense with the drive gear 18 and the rotating gear 19, the structure can be made simple, and the cost can be reduced in comparison with the first embodiment.

As described above, in accordance with the present invention, an incision can be performed by laterally oscillating the blade with a simple arrangement without providing a blade feeding mechanism on the suction ring. Further, since it is possible to prevent eyelashes or the like from biting into the feeding mechanism and suppress the scattering of abrasion dust due to the feeding mechanism and the rotating mechanism, the surgical operation can be performed smoothly.

Further, a satisfactory flap can be formed in accordance with the condition of the patient's eye by independently controlling the translation and oscillation of the blade.

Furthermore, the incision of the cornea can be performed efficiently and satisfactorily by appropriately setting the oscillation speed and the translation speed of the blade.

What is claimed is:

1. A corneal surgical apparatus for incising a cornea of a patient's eye in a layered form, comprising:
   a blade for incising for cornea;
   translating means for translating the blade in an incising direction;
   oscillating means for oscillating the blade in a perpendicular direction with respect to the incising direction;
   setting means for variably setting at least one of a translation speed and an oscillation speed of the blade; and
   determining means for determining whether or not a relationship between the translation speed and the oscillation speed is appropriate.

2. The corneal surgical apparatus according to claim 1, further comprising:
   notifying means for notifying an operator of a result of determination by said determining means.

3. The corneal surgical apparatus according to claim 2, further comprising:
   controlling means for controlling said oscillating means and said translation means on the basis of a result of determination by said determining means.

4. The corneal surgical apparatus according to claim 2, further comprising;
   storing means for storing a relative allowable setting range of the oscillation speed and the translation speed,
   wherein said determining means determines whether or not the relationship between the oscillation speed and the translation speed is appropriate on the basis of the allowable setting range stored in said storing means.

5. The corneal surgical apparatus according to claim 4, further comprising:
   displaying means for displaying the allowable setting range when it is determined by said determining means that the relationship between the oscillation speed and the translation speed is inappropriate.

6. The corneal surgical apparatus according to claim 4, further comprising:
   resetting means for resetting at least one of the oscillation speed and the translation speed on the basis of the allowable setting range when it is determined by said determining means that the relationship between the oscillation speed and the translation speed is inappropriate.

7. A corneal surgical apparatus for incising a cornea of a patient's eye in a layered form, comprising:
   a blade for incising the cornea;
   translating means for translating the blade in an incising direction;
   oscillating means for oscillating the blade in a perpendicular direction with respect to the incising direction;
   setting means for variably setting two parameters which respectively correspond to an oscillation speed of the blade defined by the oscillating means and a translation speed of the blade defined by the translating means;
   storing means for storing a relative allowable setting range of the oscillation speed and the translation speed;
   limiting means for limiting the allowable setting range of one of the parameters on the basis of both the allowable setting range stored in the storing means and the other of the parameters set by said setting means; and
   controlling means for controlling the oscillating means and the translating means on the basis of the parameters set by said setting means.

8. The corneal surgical apparatus according to claim 7, wherein said limiting means determines the allowable setting range of one of the parameters based on the other of the parameters thus set, and displays the thus determined allowable setting range.

9. The corneal surgical apparatus according to claim 7, wherein said limiting means determines the allowable setting range of one of the parameters based on the other of the parameters thus set, and permits said setting means to set the one of the parameters within the thus determined allowable setting range.

10. A corneal surgical apparatus for incising a cornea of a patient's eye in a layered form, comprising:
    a blade for incising the cornea;
    translating means for translating the blade in an incising direction;
    oscillating means for oscillating the blade in a perpendicular direction with respect to the incising direction;
    first setting means for variably setting one of two parameters which respectively correspond to an oscillation speed of the blade defined by the oscillating means and a translation speed of the blade defined by the translation means;

storing means for storing an optimum combination of the oscillation speed and the translation speed;

second setting means for setting the other of the parameters on the basis of both the combination stored in the storing means and the one of the parameters set by the first setting means; and controlling means for controlling said oscillating means and said translating means on the basis of the parameters set by the first setting means and the second setting means.

11. A corneal surgical apparatus for incising a cornea of a patient's eye in a layered form, comprising:

a main body comprising:
 a grip portion;
 a first motor provided in the main body;
 a second motor provided in the main body;
 a rotating shaft, wherein the rotating shaft is rotated about a first axis of the rotating shaft by rotation caused by the second motor;
 an eccentric shaft provided on a distal end of the rotating shaft; and
 a connecting member holding the rotating shaft in such a manner as to permit rotation of the rotating shaft about the first axis and to prohibit movement of the rotating shaft in an axial direction of the first axis with respect to the connecting member, wherein at least a part of the connecting member is translated in the axial direction together with the rotating shaft by rotation caused by the first motor, and wherein at least a part of the connecting member is held by the main body in such a manner as to permit translation of the connecting member in the axial direction and to prohibit movement of the connecting member in a perpendicular direction of the axial direction so as to guide the translation of the connecting member;

a suction ring unit, wherein the suction ring unit is fixedly attached to the main body; and a cutting unit, wherein the cutting unit is connected to the connecting member, and wherein the cutting unit is translated in the axial direction on the suction ring unit by the translation of the connecting member, the cutting unit comprising:
 a blade for incising the cornea, wherein the blade is held by the cutting unit in such a manner as to permit oscillation of the blade, and wherein the blade is translated by translation of the cutting unit and oscillated by the rotation of the rotating shaft, and
 a changing unit for changing the rotation of the rotating shaft into the oscillation of the blade, wherein the changing unit comprises an oscillation member attached to the blade, a groove provided for the oscillation member and engaged with the eccentric shaft, and a block for restricting movement of the oscillation member.

12. The corneal surgical apparatus according to claim 11, wherein the rotating shaft includes a spline shaft having a first portion circular in section and a second portion non-circular in section.

13. The corneal surgical apparatus according to claim 11, further comprising:

controlling means for controlling said first motor so as to translate the blade at a predetermined translation speed, and controlling said second motor so as to oscillate said blade at a predetermined oscillation speed.

14. The corneal surgical apparatus according to claim 13, further comprising:

setting means for variably setting at least one of the translation speed and the oscillation speed.

15. The corneal surgical apparatus according to claim 14, further comprising:

determining means for determining whether or not a relationship between the translation speed and the oscillation speed is appropriate.

16. The corneal surgical apparatus according to claim 15, further comprising:

storing means for storing a relative allowable setting range of the translation speed and the oscillation speed, wherein said determining means determines whether or not the relationship between the translation speed the oscillation speed is appropriate on the basis of the allowable setting range stored in said storing means.

17. The corneal surgical apparatus according to claim 11, further comprising:

setting means for variably setting two parameters which respectively correspond to a translation speed of the blade defined by said first motor and an oscillation speed of the blade defined by said second motor;

storing means for storing a relative allowable setting range of the translation speed and the oscillation speed;

limiting means for limiting the allowable setting range of one of the parameters on the basis of both the allowable setting range stored in said storing means and the other of the parameters set by said setting means; and controlling means for controlling said first motor and said second motor on the basis of the parameters set by said setting means.

18. The corneal surgical apparatus according to claim 11, further comprising:

first setting means for variably setting one of two parameters which respectively correspond to a translation speed of the blade defined by said first motor and an oscillation speed of the blade defined by said second motor;

storing means for storing an optimum combination of the translation speed and the oscillation speed;

second setting means for setting the other of the parameters on the basis of both the combination stored in said storing means and the one of the parameters set by said first setting means; and, controlling means for controlling said first motor and said second motor on the basis of the parameters set by said first setting means and said second setting means.

19. The corneal surgical apparatus according to claim 11, further comprising:

position detecting means for detecting a position of said blade; and controlling means for controlling at least one of a translation speed of the blade defined by said first motor and an oscillation speed of the blade defined by said second motor on the basis of position information obtained by said position detecting means.

20. The corneal surgical apparatus according to claim 11, further comprising:

changeover means for changing over at least one of a translation speed of the blade defined by said first motor and an oscillation speed of the blade defined by said second motor in association with progression of a surgical operation.

* * * * *

UNITED STATES PATENT AND TRADEMARK OFFICE
CERTIFICATE OF CORRECTION

PATENT NO.    : 6,592,601 B1
DATED         : July 15, 2003
INVENTOR(S)   : Minoru Toh et al.

It is certified that error appears in the above-identified patent and that said Letters Patent is hereby corrected as shown below:

<u>Title page,</u>
Item [57], ABSTRACT,
Lines 6 and 10, "motor" should read -- motors --.

<u>Column 13,</u>
Line 48, "incising for" should read -- incising the --.
Line 63, "claim 2," should read -- claim 1, --.

<u>Column 14,</u>
Line 1, "claim 2," should read -- claim 1, --.

<u>Column 15,</u>
Line 25, "axis and to prohibit movement of the" should read -- axis, the --.
Line 26, "shaft in" should read -- shaft being prevented from moving in --.

Signed and Sealed this

Twenty-fourth Day of February, 2004

JON W. DUDAS
*Acting Director of the United States Patent and Trademark Office*